(12) United States Patent
Filshie et al.

(10) Patent No.: US 8,100,926 B1
(45) Date of Patent: *Jan. 24, 2012

(54) SURGICAL CLIP

(75) Inventors: Marcus Filshie, Nottingham (GB);
Darren John Giddins, Nottingham (GB)

(73) Assignee: Femcare Limited (GB)

( * ) Notice: Subject to any disclaimer, the term of this patent is extended or adjusted under 35 U.S.C. 154(b) by 946 days.

This patent is subject to a terminal disclaimer.

(21) Appl. No.: 10/031,218

(22) PCT Filed: Jul. 14, 2000

(86) PCT No.: PCT/GB00/02709
§ 371 (c)(1),
(2), (4) Date: May 7, 2002

(87) PCT Pub. No.: WO01/05309
PCT Pub. Date: Jan. 25, 2001

(30) Foreign Application Priority Data

Jul. 15, 1999 (GB) .................................. 9916484.0

(51) Int. Cl.
*A61B 17/122* (2006.01)
(52) U.S. Cl. ........... 606/157; 606/151; 606/158; 24/489
(58) Field of Classification Search .................. 606/151, 606/153, 157, 158, 120, 142, 143; 24/489, 24/518–520
See application file for complete search history.

(56) References Cited

U.S. PATENT DOCUMENTS

| | | | |
|---|---|---|---|
| 1,728,322 A * | 9/1929 | Badrian .......................... 606/157 |
| 1,830,039 A * | 11/1931 | Rosicky ............................. 2/150 |
| 2,568,511 A * | 9/1951 | Ogden ........................... 24/66.8 |
| 3,270,745 A | 9/1966 | Wood |
| 3,463,156 A * | 8/1969 | Rackear et al. ............... 606/158 |
| 3,854,482 A | 12/1974 | Laugherty et al. |
| 3,926,195 A | 12/1975 | Bleier et al. |
| 4,024,868 A * | 5/1977 | Williams ....................... 606/158 |
| 4,112,944 A * | 9/1978 | Williams ....................... 604/244 |
| 4,112,951 A * | 9/1978 | Hulka et al. .................. 128/831 |
| 4,192,315 A * | 3/1980 | Hilzinger et al. ............. 606/158 |
| 4,346,869 A * | 8/1982 | MacNeill ........................ 251/10 |
| 4,418,694 A * | 12/1983 | Beroff et al. .................. 606/158 |
| 4,424,810 A | 1/1984 | Jewusiak |
| 4,476,865 A * | 10/1984 | Failla et al. ................... 606/158 |
| 4,478,218 A * | 10/1984 | Mericle .......................... 606/143 |
| 4,484,581 A * | 11/1984 | Martin et al. ................. 606/158 |
| 4,489,725 A * | 12/1984 | Casey et al. ................... 128/831 |
| 4,519,392 A * | 5/1985 | Lingua ........................... 606/151 |
| 4,579,118 A * | 4/1986 | Failla ............................. 606/158 |
| 4,589,626 A * | 5/1986 | Kurtz et al. ..................... 251/10 |

(Continued)

FOREIGN PATENT DOCUMENTS

DE 27 32 326 1/1979

(Continued)

*Primary Examiner* — Darwin Erezo
(74) *Attorney, Agent, or Firm* — Salter & Michaelson

(57) ABSTRACT

A surgical clip comprises an upper jaw (12) and a lower jaw 14), a section lining, and includes a complex shape for the upper jaw (12) comprising a first generally straight section (120) and a second shallow curved section (122) thereby enabling the clip to be inserted down a narrow magazine tube and to be able to be operable into a wide capture opening to capture larger vessels and then closed into a latched position on application of force the relatively straight section (120) and then to the shallow curved section (122).

9 Claims, 5 Drawing Sheets

U.S. PATENT DOCUMENTS

Figure 1:
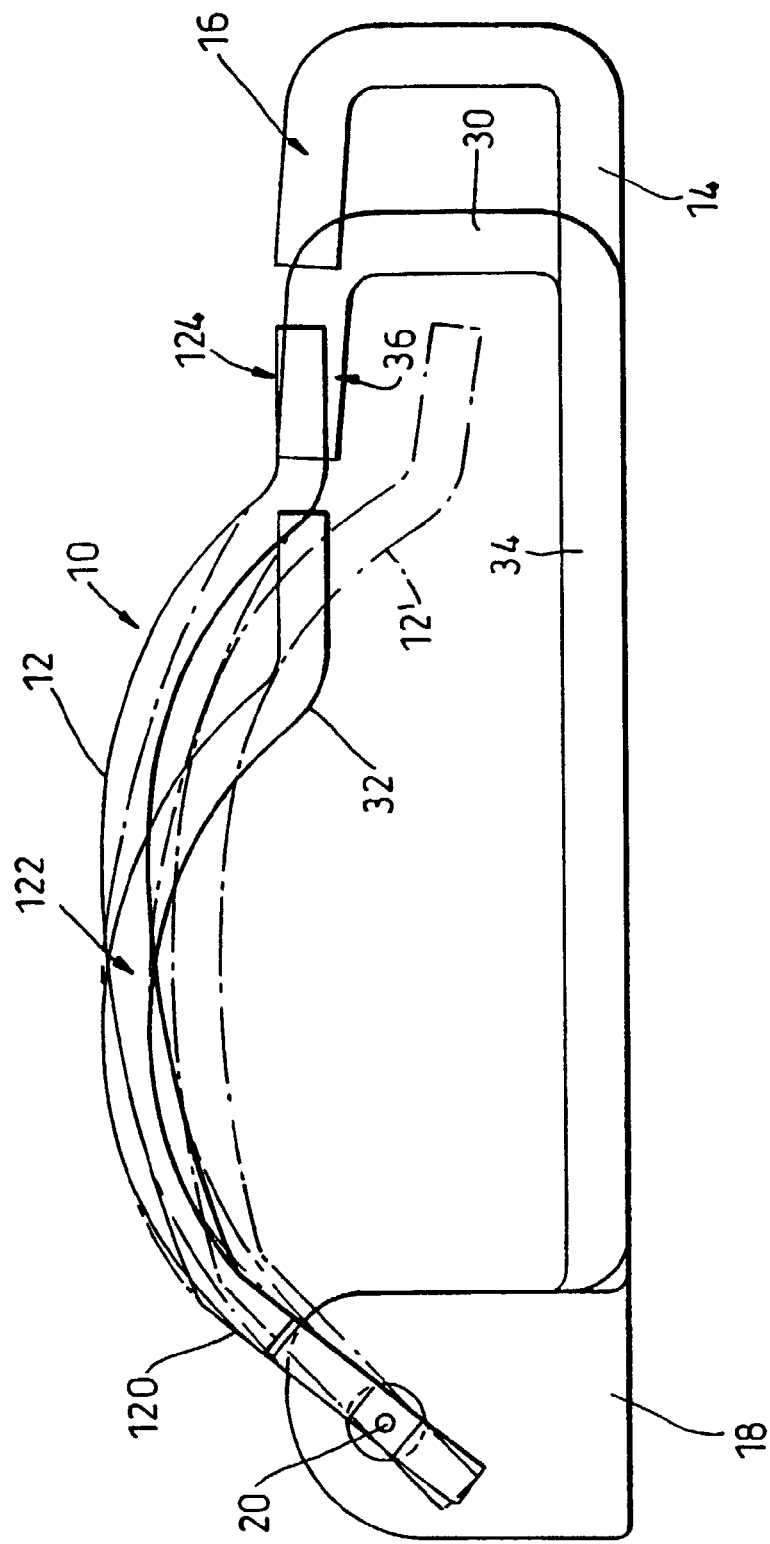

| | | | | |
|---|---|---|---|---|
| 4,620,541 | A * | 11/1986 | Gertzman et al. | 606/158 |
| 4,638,804 | A * | 1/1987 | Jewusiak | 606/158 |
| 4,702,247 | A | 10/1987 | Blake, III et al. | |
| 4,726,372 | A * | 2/1988 | Perlin | 606/158 |
| 4,733,666 | A * | 3/1988 | Mercer, Jr. | 606/151 |
| 4,777,950 | A * | 10/1988 | Kees, Jr. | 606/158 |
| 4,796,625 | A * | 1/1989 | Kees, Jr. | 606/158 |
| 4,807,622 | A * | 2/1989 | Ohkaka et al. | 606/167 |
| 4,822,348 | A * | 4/1989 | Casey | 604/346 |
| 4,942,886 | A | 7/1990 | Timmons | |
| 4,966,603 | A * | 10/1990 | Focelle et al. | 606/158 |
| 4,988,355 | A | 1/1991 | Leveen et al. | |
| 5,002,552 | A * | 3/1991 | Casey | 606/157 |
| 5,053,045 | A * | 10/1991 | Schmidt et al. | 606/157 |
| 5,160,339 | A * | 11/1992 | Chen et al. | 606/158 |
| 5,171,250 | A | 12/1992 | Yoon | |
| 5,219,353 | A * | 6/1993 | Garvey et al. | 606/157 |
| 5,282,812 | A | 2/1994 | Suarez, Jr. | |
| 5,312,426 | A * | 5/1994 | Segawa et al. | 606/158 |
| 5,354,306 | A * | 10/1994 | Garvey et al. | 606/157 |
| 5,359,993 | A | 11/1994 | Slater et al. | |
| 5,437,680 | A | 8/1995 | Yoon | |
| 5,478,003 | A | 12/1995 | Green et al. | |
| 5,507,297 | A | 4/1996 | Slater et al. | |
| 5,522,823 | A * | 6/1996 | Kuntz et al. | 606/157 |
| 5,549,619 | A * | 8/1996 | Peters et al. | 606/157 |
| 5,569,274 | A * | 10/1996 | Rapacki et al. | 606/158 |
| 5,575,802 | A * | 11/1996 | McQuilkin et al. | 606/151 |
| 5,695,505 | A | 12/1997 | Yoon | |
| 5,758,420 | A * | 6/1998 | Schmidt et al. | 29/896.9 |
| 5,843,101 | A * | 12/1998 | Fry | 606/157 |
| 5,846,255 | A * | 12/1998 | Casey | 606/157 |
| 5,849,019 | A | 12/1998 | Yoon | |
| 5,938,666 | A | 8/1999 | Reynolds et al. | |
| 6,059,799 | A | 5/2000 | Aranyi et al. | |
| 6,206,896 | B1 * | 3/2001 | Howell et al. | 606/151 |
| 6,251,117 | B1 * | 6/2001 | Kringel et al. | 606/158 |
| 6,464,710 | B1 * | 10/2002 | Foster | 606/158 |
| 6,699,258 | B1 * | 3/2004 | Sadler et al. | 606/157 |
| 2003/0074009 | A1 * | 4/2003 | Ramsey et al. | 606/120 |
| 2004/0116948 | A1 * | 6/2004 | Sixto et al. | 606/158 |

FOREIGN PATENT DOCUMENTS

| | | |
|---|---|---|
| DE | 40 15 562 | 11/1991 |
| EP | 24687 | 11/1981 |
| EP | 0087940 | 9/1983 |
| EP | 0087941 | 9/1983 |
| EP | 0 220 643 | 5/1987 |
| EP | 0 820 725 | 1/1998 |
| EP | 0 916 309 | 5/1999 |
| FR | 2 709 944 | 3/1995 |
| FR | 2709944 | 3/1995 |
| GB | 886356 | 1/1962 |
| GB | 972 731 | 10/1964 |
| GB | 1530282 | 10/1978 |
| GB | 2054384 | 2/1981 |
| GB | 2 177 748 | 1/1987 |
| GB | 2177748 | 1/1987 |
| GB | 2190297 | 11/1987 |
| GB | 2 226 958 | 7/1990 |
| GB | 2226958 | 7/1990 |
| GB | 2 243 789 | 11/1991 |
| GB | 2251794 | 7/1992 |
| GB | 2297487 | 8/1996 |
| WO | WO 91/08708 | 6/1991 |
| WO | WO 94/15537 | 7/1994 |
| WO | WO 95/13023 | 5/1995 |
| WO | WO 0105309 | 1/2001 |

* cited by examiner

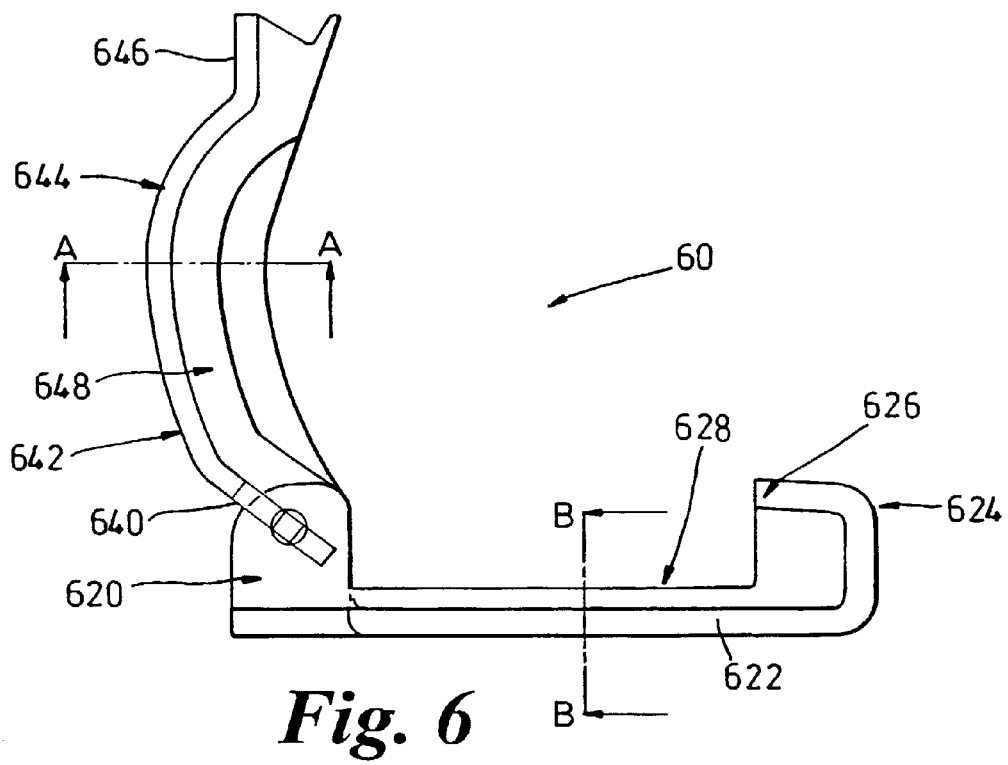
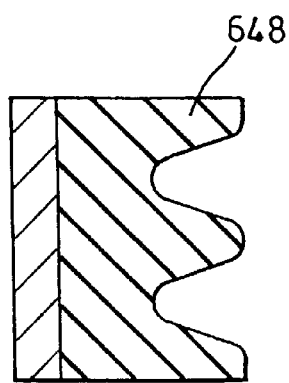
Fig. 7
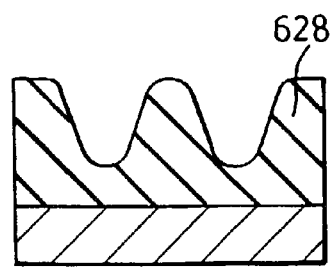
Fig. 8

SURGICAL CLIP

The present invention relates to surgical clips and more particularly to ligation clips.

During surgical procedures, it is often necessary to use several ligation clips. These can be inserted individually into a suitable applicator, but is more efficient if several clips can be loaded into an applicator preferably in a replaceable magazine.

U.S. Pat. No. 5,219,353 discloses a surgical endoclip comprising a generally U-shaped clip comprising a thin metallic unitary member and including a latch member incorporated in a lower section of the clip.

GB 2177748-A discloses a Filshie clip having upper and a lower jaw members which are connected by a hinge and including co-operating latching means on said upper and lower jaw members the upper jaw member being curved.

The present invention has for a first object to provide a clip in particular suitable as a ligation clip which can be loaded into a relatively narrow diameter magazine for delivering such clips down a tube which may be inserted down a cannula.

During surgical procedures, ligation clips can be extensively used; several may be applied to various anatomical structures in the course of one operation.

State of the art clips are limited to the use on anatomical structures up to 5 mm in diameter after which their effectiveness becomes impaired.

It is the object of this invention to provide a ligation clip that can be used on anatomical structures up to and in excess of 5 mm in diameter.

In particular, the object of the invention is to provide a surgical clip that can be loaded into a dedicated applicator (incorporating a magazine) for delivery down a narrow cannula.

The increased effectiveness in dealing with larger structures will mean that the simpler clipping technique can be used instead of ligature sutures that require a longer training curve and take longer to apply thus simplifying the equipment required.

In addition the increased effectiveness of clipping means that only the smallest number of clips required needs to be used; this will reduce the degree of intervention necessary.

The clip is designed to be able to be loaded into the magazine of the applicator shaft (in multiples of two to ten). The applicator shaft or barrel incorporating different multiples of clips may be disposable.

The geometry of the upper jaw of the clip is critical when having to occlude anatomical structures greater than 5 mm in diameter. The upper jaw must be able to withstand deformation whilst occluding a structure until the upper jaw is safely within the confines of the latch (opposite end to the hinge).

In addition the geometry of the upper jaw also allows for the increased capacity for occlusion that is necessary when occluding larger structures.

If the cannula can be made to a large diameter then the design of the clip can be relatively simple but as the diameter of the cannula is reduced then the clip design must be more complex in order to be able to provide an elongate magazine to enable the clips firstly to be fed down the cannula, secondly to be able to be openable once it has emerged from the magazine and thirdly to be able to be lockable by the applicator to effect closure of a blood vessel. A mere enlargement of existing clip design may not achieve a satisfactory locking procedure for the enlarged clip.

It is an object of the present invention to provide a surgical clip which can occlude larger structures and also which can preferably be inserted into a narrow applicator for subsequent insertion down a narrow cannula.

In a specific example the cannula can be less than 7 mm in diameter and in to a preferred example it can be less than 5 mm in diameter.

The present invention provides a surgical clip as claimed in Claim 1.

In a preferred embodiment, the arcuate section comprises a third generally straight section adjacent to said curved section at the opposite end of the upper jaw to the large section said substantially straight section, when in the closed position of the clip interlocking under the latching section of the lower jaw.

Figure 2:
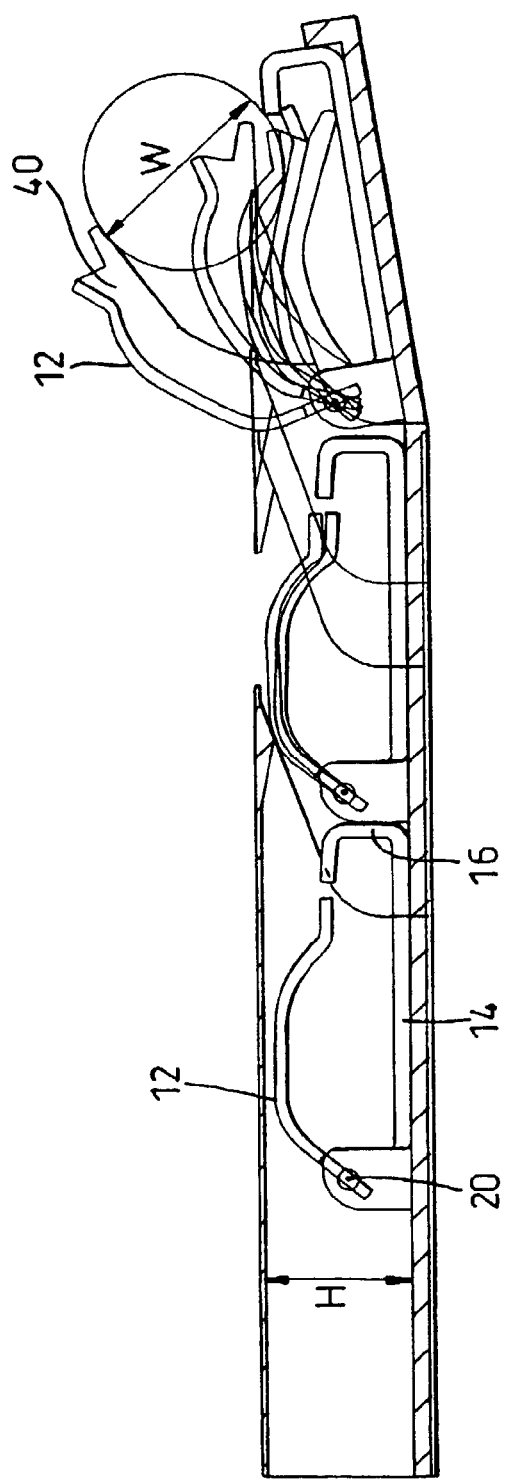
Figure 3:
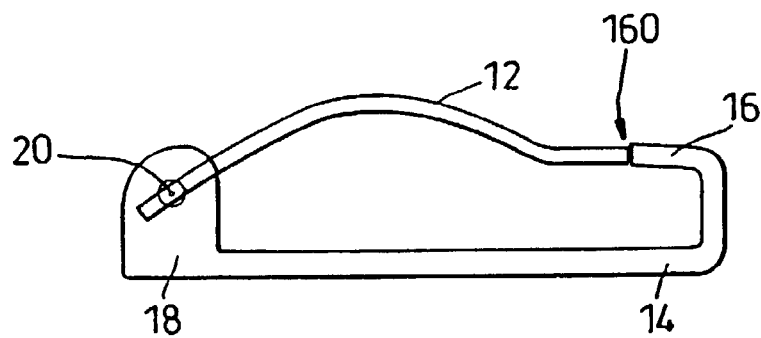
Figure 4:
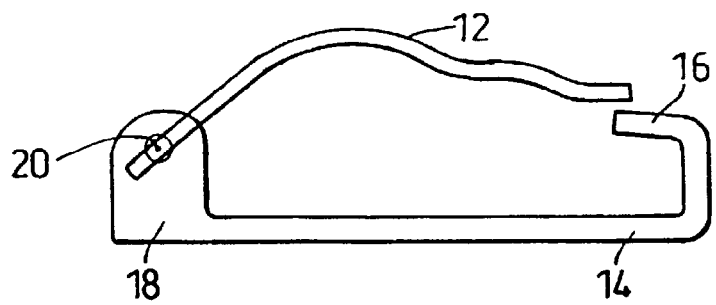
Figure 5:
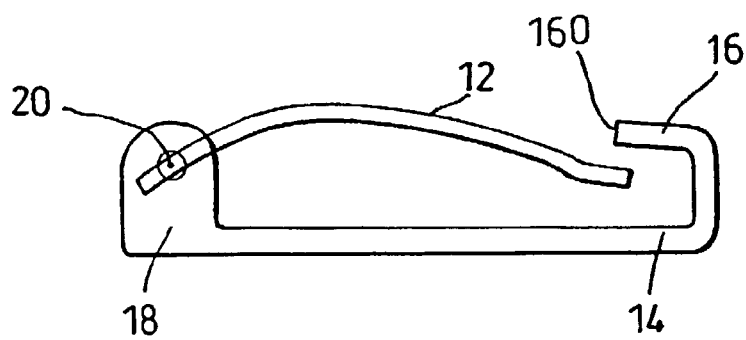
Figure 9:
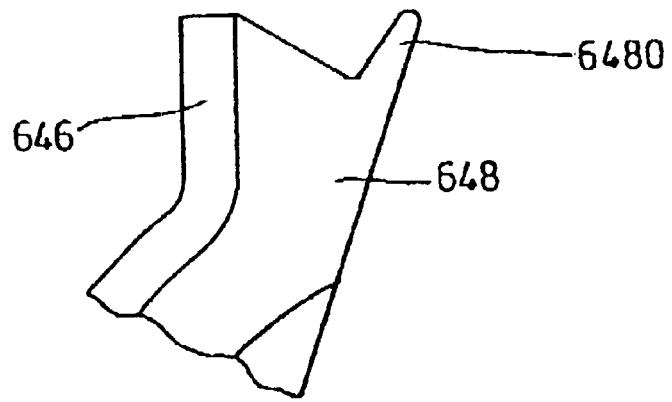
Figure 10:
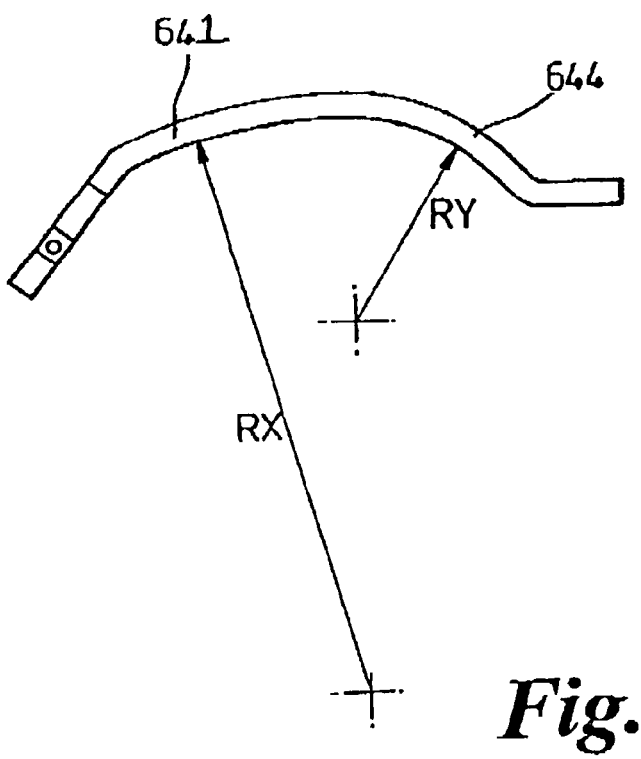

Embodiments of the present invention will now be described, by way of example with reference to the accompanying drawings in which:

FIG. 1 shows an enlarged side elevation view of a first clip in accordance with the present invention, the figure also showing by way of comparison a side elevation view of a known sterilisation clip;

FIG. 2 shows diagrammatically a longitudinal cross-section of a part of an applicator illustrating the portion of the clip of the present invention in a magazine section of the applicator and also in the operable position in which position the clip is closed, as to illustrated, FIGS. 3 to 5 diagrammatically illustrate the advantageous design of the clip of the present invention during closure, FIG. 6 shows an enlarged side elevation view of a second clip in accordance with the present invention, FIG. 7 shows a cross sectional view on line 'A-A' of FIG. 6 illustrating the cross sectional shape of the silicone rubber lining of the upper jaw of the clip, FIG. 8 shows a cross sectional view on line 'B-B' of FIG. 6 illustrating the cross sectional shape of the silicone rubber lining of the lower jaw of the clip, FIG. 9 shows a detail of the end, closure section of the upper jaw of the clip of FIG. 6 and FIG. 10 shows the upper jaw of the clip of FIG. 6 in greater detail.

With reference to FIG. 1, a clip 10 according to the present invention is shown in side elevation.

The clip comprises an upper jaw section 12 and a lower jaw section 14. The lower jaw section has a latch portion 16 at one end and a hinge portion 18 at the other end. The latch portion 16, as illustrated in FIG. 1, includes a reversed segment that is substantially shorter in length than the length of the elongated substantially straight piece of the lower jaw section 14.

The upper jaw 12 is hinged by a hinge pin 20 to the lower jaw.

The upper jaw 12 comprises at least two shaped sections. A first section 120 comprises a relatively straight short section and the second section 122 comprises a relatively gently curved section.

A third section 124 comprising a co-operating latch portion may be provided at the end of the upper jaw opposite to the hinge 18.

In a practical clip (see FIG. 2) one or both jaws 12, 14 will be provided with a silicone rubber lining but this is not shown in FIG. 1 for ease of viewing.

The jaw 12 is shown in a second position 12' to illustrate movement of the jaw which is further illustrated in FIG. 2.

By way of contrast, a known sterilisation clip 30 (the Filshie clip—see GB Patent Application No. 2177748A) is shown in FIG. 1 having a bottom jaw 34 and top jaw 32 and using the same hinge 18. The latch portion 36 can be seen to be substantially nearer to the hinge 18 than the latch portion 16 of the clip according to the present invention.

The top jaw 32 is as shown a substantially constant curve.

The advantage of the clip design according to the present invention is that the straight section and shallow curve allows the clip (see FIG. 2) to pass down (or be fed down) a relatively narrow diameter (H) tube and also to then open to provide an opening (capture) width W which is substantially greater than the height H even with the presence of the silicone rubber lining 40.

The straight section 120 in combination with the shallow curve section operates in a manner which is particularly advantageous with a slightly longer clip. The original Filshie clip provides an overall clip length of approximately 14 mm but the new clip can be 16 mm or greater.

If the original clip design were to be made longer then the upper jaw would be a longer arcuate curve. When pressure is applied to this curve, the upper jaw will deform but the combination of longer jaw and the silicone lining may cause the upper jaw end section 124 to either completely fail to enter under the latch section 16 (FIG. 4) or possibly to meet against the end position 160 (FIG. 3) and not slide under the latch.

In the first case, the surgeon will be aware that the clip has failed but in the second case FIG. 3 the surgeon may assume that correct closure has occurred but the clip will fail at a later stage due to the pressure exerted by the silicone rubber lining after the operation has been completed.

With the present design of the upper jaw, with the initial straight section it can be seen in FIG. 5 that the jaw when distorted by the applicator fits within the latch because the initial closing pressure is on the straight section and thus the initial pressure does not distort the curved section until the end portion 124 (FIG. 1) has been depressed towards the lower jaw 14.

FIG. 6 shows an alternative design clip 60 comprising a lower jaw 622 and an upper jaw 642. As in FIG. 1 the lower jaw comprises a hinge portion 620 an elongate relatively straight portion 640 and a latch portion 646.

The upper jaw 642 comprises four separate straight and arcuate sections. A first substantially straight portion 640, a second arcuate portion 641 having a radius RX (FIG. 10) and a third arcuate portion 644 having a radius RY (FIG. 10) and a fourth substantially straight section 646.

At the distal end from hinge section 620 the portion 646 is provided to latch under lip 626.

The clip 60 is preferably lined with silicone rubber linings 628 and 648 respectively attached to the lower and upper jaws 622, 642.

The profiles of the linings 628, 648 are shown respectively in FIGS. 7 and 8 and comprise a sinusoidal shape on the internal surface. This shape provides the desired property of the silicone rubber lining of being able to grip the vessel to be occluded whilst still being able to exert the necessary occlusion force when the clip has been closed.

With reference now to FIG. 9 the end section 646 (FIG. 6) of the upper jaw comprises a relatively short straight section and the silicone rubber lining is provided with a tongue 6480 which is relatively thin in comparison with the rest of the lining 648.

The tongue 6480 serves to initially capture the vessel to be occluded providing in effect an extension to the upper jaw. Because the tongue 6480 is relatively thin it is readily squashed into the silicone rubber lining 628 of the lower jaw thereby not preventing closure of the clip.

With reference now to FIG. 10 in order to effect satisfactory closure of the clip whilst allowing the clip to pass down a relatively small diameter tube the upper jaw of the clip is provided with a first substantially straight portion 640 at the proximal end nearest the hinge as in the embodiment of FIG. 6.

In this embodiment the upper jaw is then provided with two arcuate sections 641 and 644.

Arcuate section 641 has a radius of curvature RX much larger than that of section 644 (R2). In a specific embodiment the radius of arcuate of RX is 11.9 mm and that of RY is 4.6 mm.

The use of two different radii in combination with the straight section allows the clip in this embodiment to be fed down a small diameter tube in a semi closed position to be openable at the end of the tube and to then be latched without risk of the upper jaw being distorted when the latching pressure is applied.

The invention claimed is:

1. A surgical clip, comprising:
   an elongate upper jaw having a proximal end and a distal end, and an elongate lower jaw having one and other ends;
   a hinge member that supports at a base thereof the one end of the elongated lower jaw;
   said elongated lower jaw including an elongated substantially straight piece extending from said base, and at the other end thereof a reversed segment contiguous with said elongated substantially straight piece and forming a latch for engagement with the upper jaw;
   said reversed segment being substantially shorter in length then the length of said elongated substantially straight piece;
   said hinge member including a hinge pin disposed over the base of the hinge member and spaced from and over the one end of the elongated lower jaw;
   said elongated upper jaw including, at the proximal end thereof, a proximal straight section supported for pivoting at the hinge pin, and an arcuate shaped section contiguously adjoining the proximal straight section and extending distally thereof and away from the hinge pin;
   said arcuate shaped section including a first arcuate shaped portion contiguous with said proximal straight section and a second arcuate shaped portion contiguous with said first arcuate shaped portion disposed at an opposite end of said first arcuate shaped portion to said proximal straight section;
   said elongated upper and lower jaws having respective facing surfaces;
   said first arcuate shaped portion having a first radius of curvature in its facing surface that is greater than a radius of curvature of said second arcuate shaped portion which has a second radius of curvature in its facing surface;
   wherein the first and second arcuate shaped portions are both defined in the facing surface of the upper jaw;
   wherein the first radius of curvature and the second radius of curvature are both defined by respective centers of curvature located on a side of the upper jaw having the facing surface;
   a distal straight section contiguous with said second arcuate shaped portion and disposed at the opposite end of said second arcuate shaped portion to the hinge pin;
   said distal straight section having a free end that extends in a direction distally of said hinge pin.

2. A surgical clip as claimed in claim 1 in which said first radius of curvature is of the order of three times that of the second radius of curvature.

3. A surgical clip as claimed in claim 1 wherein the surgical clip has open and closed positions, and wherein the reverse segment has a straight free end that extends substantially in line with the distal straight section in the closed position of the surgical clip.

4. A surgical clip as claimed in claim 1 wherein, when the upper jaw is distorted it fits within the latch because an initial closure pressure is imposed on the straight section and thus the initial pressure fails to distort the arcuate shaped section until the free end has been depressed toward the lower jaw.

5. A surgical clip as claimed in claim 1 wherein the jaws are provided with a silicone rubber lining on either the upper or lower jaw or both jaws, and in combination with a clip closure member wherein an initial closure pressure is imposed by the closure member on the proximal straight section.

6. A surgical clip as claimed in claim 1 wherein the total length of the first and second arcuate shaped portions is greater than the length of the proximal straight section.

7. A surgical clip as claimed in claim 1 wherein the first arcuate shaped portion is contiguous with the second arcuate shaped portion forming a complex contiguous curved shape.

8. A surgical clip as claimed in claim 1 wherein said second arcuate shaped portion has an arcuate surface on both an outer contact surface thereof and the facing surface of the upper jaw thereof.

9. A surgical clip as claimed in claim 1 wherein the length of the first arcuate shaped portion is greater than the length of the second arcuate shaped portion.

\* \* \* \* \*